United States Patent
Funahashi et al.

(10) Patent No.: US 6,852,836 B1
(45) Date of Patent: Feb. 8, 2005

(54) GENE ENCODING BRAIN-SPECIFIC MEMBRANE PROTEIN

(75) Inventors: Shin-Ichi Funahashi, Ibaraki (JP); Shoji Miyata, Ibaraki (JP); Nobuo Nomura, Chiba (JP); Takahiro Nagase, Chiba (JP); Osamu Ohara, Chiba (JP)

(73) Assignees: Chugai Sieyaku Kabushiki Kaisha, Tokyo (JP); Kazusa DNA Research Institute, Chiba (JP)

( * ) Notice: Subject to any disclaimer, the term of this patent is extended or adjusted under 35 U.S.C. 154(b) by 0 days.

(21) Appl. No.: 09/831,846

(22) PCT Filed: Nov. 18, 1999

(86) PCT No.: PCT/JP99/06449

§ 371 (c)(1),
(2), (4) Date: Aug. 21, 2001

(87) PCT Pub. No.: WO00/31256

PCT Pub. Date: Jun. 2, 2000

(30) Foreign Application Priority Data

Nov. 20, 1998 (JP) .......................................... 10/331727

(51) Int. Cl.⁷ .............................................. C07K 14/47
(52) U.S. Cl. ....................................... 530/350; 530/395
(58) Field of Search ............................... 530/300, 350, 530/395

(56) References Cited

PUBLICATIONS

Adams et al., "Rapid cDNA sequencing (expressed sequence tags) from a directionally cloned human infant brain cDNA library", Nature Genetics, 4:374–380, 1993.

Dong et al., "GRIP: a synaptic PDZ domain–containing protein that interacts with AMPA receptors", Nature, 386:279–284, 1997.

Nagase et al., "Prediction of the Coding Sequences of Unidentified Human Genes. XV. The Complete Sequences of 100 New cDNA Clones from Brain Which Code for Large Proteins in vitro", DNA Res., 6:337–345, 1999.

Poulat et al., "The Human Testis Determining Factor *SRY* Binds a Nuclear Factor Containing PDZ Protein Interaction Domans", J. Biol. Chem., 272(11):7167–7172, 1997.

*Primary Examiner*—Gary Kunz
*Assistant Examiner*—Stephen Gucker
(74) *Attorney, Agent, or Firm*—Fish & Richardson P.C.

(57) ABSTRACT

A novel gene apparently encoding a transmembrane glycoprotein has been successfully isolated by constructing a cDNA library of 4 kb or above in size from mRNA expressed in human adult brain and analyzing the structures of cDNAs contained within said library by the shotgun method. The novel gene shows brain-specific expression and the protein encoded by said gene has a typical PDZ protein binding motif.

4 Claims, 3 Drawing Sheets

[Fig. 1]
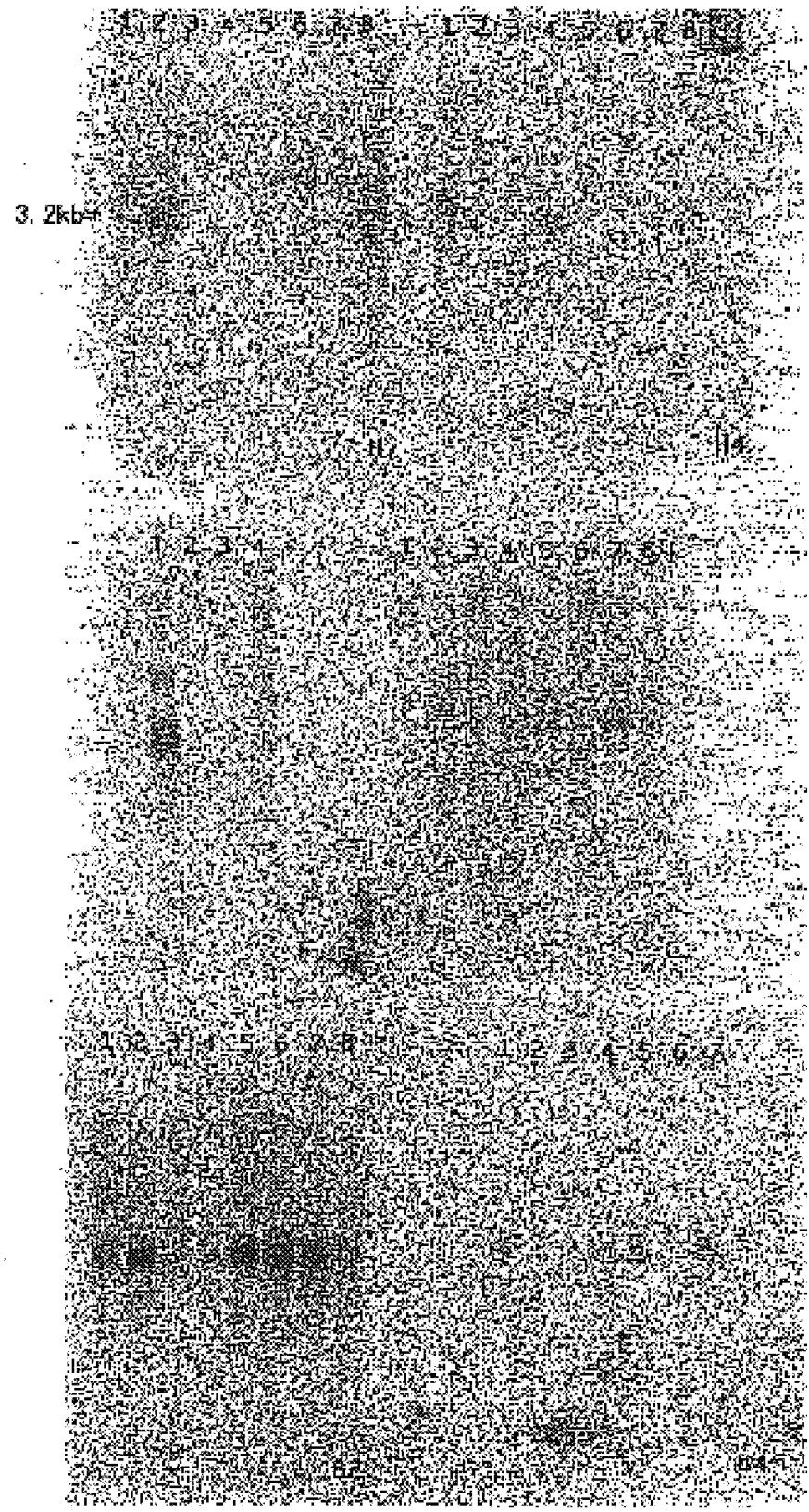

[Fig. 2]

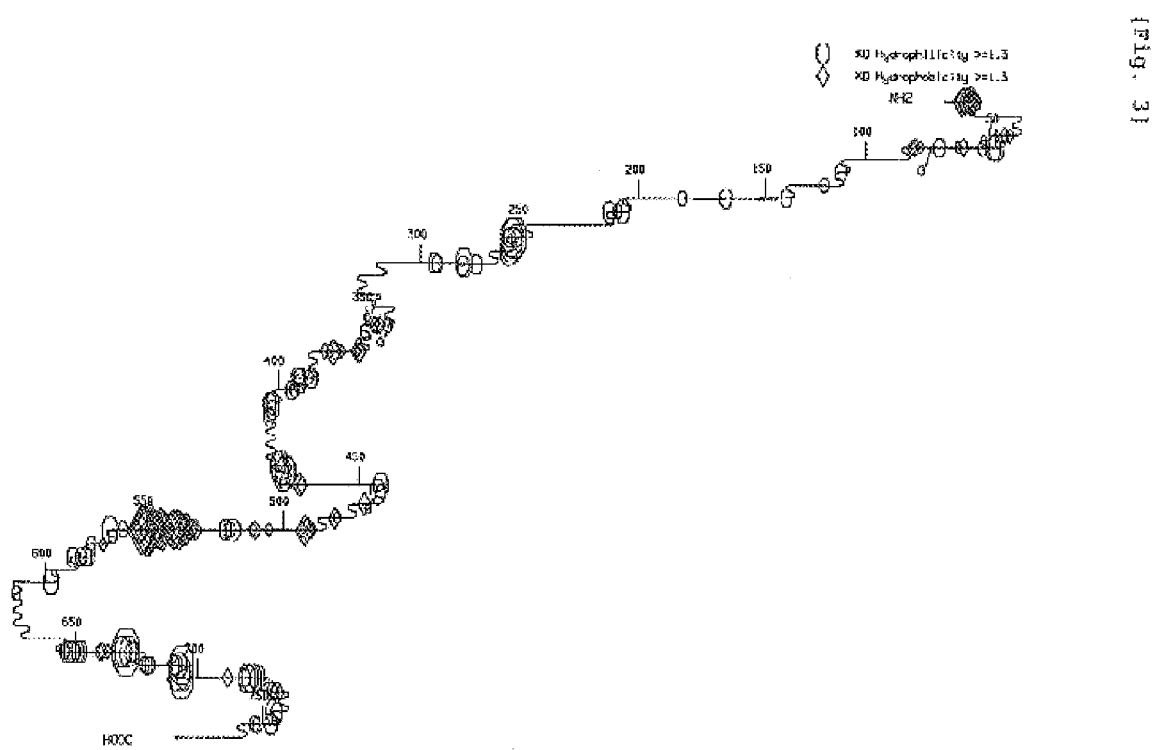

GENE ENCODING BRAIN-SPECIFIC MEMBRANE PROTEIN

TECHNICAL FIELD

The present invention relates to a novel membrane protein specifically expressed in the brain, a nucleic acid molecule encoding the protein, and methods of preparing and using same.

BACKGROUND ART

A variety of cells present in the nerve system form a nerve network that supports high-level brain functions. Elucidation of mechanisms of differentiation, development and apoptosis of the nerve system is an important research subject, to deepen our understanding of functions of nerve system or critical mechanisms of nerve-related disorders. Thus, researches in this field have been energetically pursued.

Recently, a number of novel signal transducer molecules, including the PDZ protein, have been discovered one after another, as indicated by reports on the complex formation of receptors or ion channel molecules with the PDZ proteins such as PSD95/SAP90 in the post-synapse density (PSD) of postsynaptic membrane to perform the signal transduction (Science 269, 1737–1740 (1995), Nature 378, 85–88 (1995), Neuron 17, 103–113 (1996), Neuron 17, 255–265 (1996), J. Neurosci. 16, 2157–2163 (1996), Nature 386, 223, 239 (1997), TIBS 21, 455–458 (1996), J. Yanagisawa et al. (1997) J. Biol. Chem. 272, 7167–7172).

PDZ proteins are thought to serve as modular proteins in the formation of a protein complex, which transmits signals from outside to inside of cells and is as compact as possible. Thus, such proteins play an important role in the complex signal transduction of the nerve system.

On the other hand, glycoproteins present on the cell membrane are expected to function as the receptor to receive such external signals. Thus, there has been a high demand for the isolation and analysis of these membrane proteins for elucidating signal transduction mechanisms in the brain.

DISCLOSURE OF THE INVENTION

The present invention aims to provide a novel membrane protein which is specifically expressed in the brain, a nucleic acid molecule encoding the protein, and a method for manufacturing these compounds as well as the use thereof.

Present inventors have constructed a cDNA library of 4 kb or above in size from mRNA expressed in the human adult brain, and analyzed the structures of cDNAs contained in the library by the shotgun method, resulting in the successful isolation of a novel gene designated as "hh00149".

A protein encoded by the gene had a signal sequence comprising 20 amino acids, a hydrophobic amino acid region which is thought to be a transmembrane domain, and further six binding sites for asparagine-bound sugar chain, indicating that this protein is one of transmembrane glycoproteins.

Northern blot analysis indicated that the hh00149 gene showed brain-specific expression. Furthermore, the hh00149 protein was found to have a typical PDZ protein-binding motif comprising "serine-threonine-valine" at its carboxyl end, indicating the presence of a PDZ protein as its binding protein. A variety of proteins have been hitherto known to bind to the PDZ protein, including the ion channel, glutamate receptor, tumorigenic transformation-related gene product, cell adhesion molecule, membrane-associated guanylate kinase, differentiation suppressing protein, etc. (Kornau, H.-C. et al. (1995) Science 269, 1737–1740; Kim, E. et al. (1995) Nature 378, 85–88, Matsumine et al. (1996) Science 272, 1020–1023, Axelrod, J. D., et al. (1996) Science 271, 1826–1832, J. Yanagisawa et al., J. Biol. Chem. 272, 7167–7172 (1997), H. Dong et al. (1997) Nature 386, 279–284), participating in various signal transduction pathways.

From such tissue-specific expression of its gene and its structural characteristics, the hh00149 protein has been suggested to function as a signal transducer molecule from the outside to the inside of nerve cells.

This invention relates to a novel membrane protein specifically expressed in the brain, a nucleic acid molecule encoding the protein, and methods of preparing and using these compounds. More specifically, the invention provides the following:

(1) a DNA selected from the group consisting of the following (a) through (e):
  (a) a DNA encoding a protein comprising the amino acid sequence set forth in SEQ ID NO: 2;
  (b) a DNA comprising the coding region of the base sequence set forth in SEQ ID NO: 1;
  (c) a DNA encoding a protein comprising the amino acid sequence set forth in SEQ ID NO: 2, which is modified by deletion and/or addition of one or more amino acid residues, and/or substitution with other amino acids, and functionally equivalent to the protein comprising the amino acid sequence set forth in SEQ ID NO: 2;
  (d) a DNA hybridizing to the DNA comprising the base sequence set forth in SEQ ID NO: 1, and encoding a protein functionally equivalent to the protein comprising the amino acid sequence set forth in SEQ ID NO: 2; and
  (e) a DNA comprising a DNA according to any of (a) through (d) and a DNA encoding other peptide or polypeptide, encoding a fusion protein;
(2) a vector inserted with the DNA according to (1);
(3) a transformant carrying the DNA according to (1) or the vector according to (2);
(4) a protein encoded by the DNA according to (1);
(5) a method for producing the protein according to (4), said method comprising the steps of culturing the transformant according to (3) and recovering the expressed protein from said transformant or the culture supernatant thereof;
(6) an antibody binding to the protein according to (4);
(7) a method of screening for a compound which binds to the protein according to (4), said method comprising the steps of:
  (a) bringing the protein according to (4) into contact with a sample to be tested, and
  (b) selecting a compound having the activity to bind to the protein according to (4);
(8) a method for detecting or measuring the protein according to (4), said method comprising the steps of bringing the antibody according to (6) into contact with a test sample that putatively contains the protein according to (4), and detecting or measuring the formation of an immune complex of said antibody with said protein; and
(9) a polynucleotide hybridizing to the DNA comprising the base sequence according to SEQ ID NO: 1 or a complementary strand thereof and having a chain length of at least 15 bases.

The base sequence of the hh00149 cDNA isolated by the present inventors is shown in SEQ ID NO: 1, and amino acid sequence of the hh00149 protein encoded by the cDNA is shown in SEQ ID NO: 2.

The hh00149 protein of this invention has a region of sequential hydrophobic amino acids, thought to be a signal sequence, in the amino terminal 20 amino acid residues, and another hydrophobic region, which is presumed to be a transmembrane domain, located about ⅔ from the amino terminal (cf. Example 6, FIG. 3), indicating that this protein is present as a transmembrane type protein on the cell membrane. In addition, the transcriptional product of the hh00149 gene has been brain-specifically detected (cf. Example 5, FIG. 2). These facts suggest that the hh00149 protein functions especially in the brain as a signal transducer molecule to transduce a signal from the outside to the inside of cells. Therefore, the hh00149 protein can be applied to the screening of novel signal transmitters, including nerve peptides, with an expectation of its utilization in the development of remedies and diagnostics for nerve-related disorders.

The present invention also includes proteins functionally equivalent to the above-described hh00149 protein. In this invention, the term "functionally equivalent" refers to those proteins having a biological activity equivalent to the hh00149 protein. It has been demonstrated, from the analysis of binding protein using the two-hybrid system, that the hh00149 protein binds to the "149Y2H#151" protein (Japanese Patent Application No. Hei 10-331701). Therefore, the biological activity of the hh00149 protein includes its binding activity to the "149Y2H#151" protein. In addition, a binding sequence to the PDZ protein has been detected in the hh00149 protein, suggesting the presence of PDZ proteins capable of binding to the hh00149 protein. Therefore, the biological activity of the hh00149 protein also includes its binding activity to PDZ proteins. Binding activity between proteins can be detected using, for example, the following analytical methods, such as the immunoprecipitation method and two-hybrid system of yeast.

A method for inducing mutation into the amino acid sequence of protein can be used as the method for obtaining proteins functionally equivalent to the hh00149 protein. For example, a predetermined mutation can be induced into the amino acid sequence of a protein by the method of site-specific mutagenesis, using synthetic oligonucleotide primers (Kramer, W. and Fritz, H. J. Methods in Enzymol. (1987) 154, 350–367). Mutation in the amino acid sequence can also be induced using the site-specific mutagenesis system by PCR (GIBCO-BRL). It is possible, by these methods, to obtain proteins having the amino acid sequence of the hh00149 protein (SEQ ID NO: 2) which is modified by deletion or addition of one or a plurality of amino acid residues and/or substitution with other amino acid residues, without affecting its biological activity, and functionally equivalent to the hh00149 protein. Mutation of amino acids in proteins can also occur spontaneously. Such proteins, the amino acid sequence of which are artificially or spontaneously altered, are also included in the proteins of this invention.

Specifically, proteins functionally equivalent to the hh00149 protein are exemplified by those comprising the amino acid sequence set forth in SEQ ID NO: 2 from which one or more, preferably from two to thirty, more preferably from two to ten amino acid residues are deleted, or to which one or more, preferably from two to thirty, more preferably from two to ten amino acid residues are added, or in which one or more, preferably from two to thirty, more preferably from two to ten amino acid residues are substituted with other amino acids.

It is known that a protein having an amino acid sequence which is modified by deletion or addition of one or a plurality of amino acid residues and/or substitution of one or a plurality of amino acid residues with other amino acids can still retain its original biological activity (Mark, D. F. et al., Proc. Natl. Acad. Sci. USA (1984) 81, 5662–5666, Zoller, M. J. & Smith, M. Nucleic Acids Research (1982) 10, 6487–6500, Wang, A. et al., Science 224, 1431–1433, and Dalbadie-McFarland, G. et al., Proc. Natl. Acad. Sci. USA (1982) 79, 6409–6413).

A protein with one or a plurality of amino acid residues deleted is exemplified by, for example, the hh00149 protein in the form deprived of its signal peptide. On the other hand, a protein with one or a plurality of amino acid residues added is exemplified by, for example, a fusion protein containing the hh00149 protein. A fusion protein in this case is a protein consisting of the hh00149 protein fused to other peptide or protein, and is included in this invention. A fusion protein can be prepared using known techniques, by ligating the DNA encoding the hh00149 protein to another DNA encoding other peptide or protein so as to be in the same reading frame, transferring the chimeric DNA to an expression vector followed by expressing it in host cells. There is no particular limitation in the type of other peptides or proteins used for the fusion to the protein of this invention.

For example, known peptides used for fusion include FLAG (Hopp, T. P. et al., BioTechnology (1988) 6, 1204–1210), 6× His comprising six histidine (His) residues, 10× His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, etc. Proteins to be used include, for example, glutathione-S-transferase (GST), influenza hemagglutinin (HA), immunoglobulin constant region, β-galactosidase, MBP (maltose-binding protein), etc.

The protein of this invention includes a protein which is encoded by a DNA hybridizing under stringent conditions to the DNA consisting of the base sequence set forth in SEQ ID NO: 1, and functionally equivalent to the hh00149 protein. Stringent hybridization conditions can be appropriately selected by those skilled in the art, and are exemplified by, for example, low stringent conditions. Low stringent conditions are, for example, at 42° C. in 2× SSC and 0.1% SDS, and preferably at 50° C. in 2× SSC and 0.1% SDS. More preferably, high stringent conditions may be selected, which are, for example, at 65° C. in 2× SSC and 0.1% SDS. Under these conditions, as the hybridization temperature is elevated, DNA with a higher homology can be obtained.

Proteins which are functionally equivalent to the hh00149 protein, and are homologous to the protein (SEQ ID NO: 2) are also included in this invention. Herein, a "homologous protein" is one that has at least 70% or more, preferably at least 80% or more, more preferably at least 90% or more, and further more preferably at least 95% or more of amino acid sequence identity to that set forth in SEQ ID NO: 2. Sequence homology of proteins can be determined according to algorithm described in a literature (Wilbur, W. J. and Lipman, D. J. Proc. Natl. Acad. Sci. USA (1983) 80, 726–730).

The protein of this invention may be prepared by incorporating the DNA thus obtained into an expression vector, so as to be expressible under the regulation of the expression-regulating region, for example, enhancer/promoter. Then, host cells are transformed with this expression vector to express the protein.

More specifically, the process may be performed as follows. When mammalian cells are used, a commonly used useful promoter/enhancer, a DNA encoding the protein of this invention, a DNA to which the poly A signal is functionally linked downstream of the 3'-terminal of the above-described DNA or a vector containing these elements is constructed. A promoter/enhancer is exemplified by, for example, the human cytomegalovirus immediate early promoter/enhancer.

In addition, other promoter/enhancer usable for protein expression includes the viral promoter/enhancer of retrovirus, polyoma virus, adenovirus, simian virus 40 (SV40), and such, and a promoter/enhancer derived from mammalian cells, such as the human elongation factor 1α (HEF1α).

For example, protein expression can be easily carried out according to the method of Mulligan et al. (Nature (1979) 277, 108) when the SV40 promoter/enhancer is used, or the method of Mizushima et al. (Nucleic Acids Res. (1990) 18, 5322) when the HEF1α promoter/enhancer is employed.

When $E.\ coli$ is used, proteins can be easily expressed by functionally ligating a commonly used useful promoter and signal sequence for the polypeptide secretion to a gene to be expressed. In this case, the promoter may be, for example, the lacZ promoter or the araB promoter. Protein expression may be achieved according to the method of Ward, et al. (Nature (1998) 341, 544–546; FASAB J. (1992) 6, 2422–2427) when the lacZ promoter is used, or the method of Better et al. (Science (1988) 240, 1041–1043) when the araB promoter is employed.

When a protein is to be produced in the periplasm of $E.\ coli$, the pelB signal sequence (Lei, S. P. et al., J. Bacteriol. (1987) 169, 4379) may be used as a protein secretion signal.

Replication origins derived from SV40, polyoma virus, adenovirus, bovine papilloma virus (BPV) and such, can also be used. Furthermore, to amplify the gene copy number in the host cell system, expression vectors may contain genes such as an aminoglycoside transferase (APH) gene, a thymidine kinase (TK) gene, a gene encoding xanthine-guanine phosphoribosyltransferase of $E.\ coli$ (Ecogpt) and a dihydrofolate reductase (dhfr) gene, as selective markers.

Any expression vector may be used to produce the protein of this invention so long as they are preferably used in this invention. Expression vectors used in this invention include those derived from mammals such as pEF and pCDM8, (those derived) from insect cells such as pBacPAK8, (those derived) from plants such as pMH1 and pMH2, (those derived) from animal viruses such as pHSV, pMV and pAdexLcw, (those derived) from retroviruses such as pZIpneo, (those derived) from yeast such as pNV11 and SP-Q01, (those derived) from $Bacillus\ subtilus$ such as pPL608 and pKTH50, and (those derived) from $E.\ coli$ such as pQE, pGEAPP, pGEMEAPP and pMALp2.

Expression vectors of this invention constructed as described above are transferred to host cells using known methods, for example, the calcium phosphate method (Virology (1973) 52, 456–467), the electroporation method (EMBO J. (1982) 1, 841–845), and the like.

In this invention, any production systems can be used for the protein manufacturing. For the protein production, there are in vitro and in vivo production systems. The in vitro production systems include those using eukaryotic cells and prokaryotic cells.

When eukaryotic cells are used, there are protein production systems using cells of animals, plants or fungi. Animal cells commonly used are mammalian cells, for example, CHO cell (J. Exp. Med. (1995) 108, 945) COS cell, myeloma cell, BHK (baby hamster kidney) cell, HeLa cell and Vero cell, amphibian cells, for example, oocytes of $Xenopus\ laevis$ (Valle, et al., Nature (1981) 291, 358–340) or insect cells, for example, sf9, sf21 and Tn5 cells. Of CHO cells, especially those deficient of the DHFR gene, dhfr-CHO cell (Proc. Natl. Acad. Sci. USA (1980) 77, 4216–4420) and CHO K-1 cell (Proc. Natl. Acad. Sci. USA (1968) 60, 1275), are preferably used.

Known plant cells used for protein production are those derived from $Nicotiana\ tabacum$, which can be cultured as callus. Fungus cells commonly used include yeast, belonging to, for example, the genus $Saccharomyces$ such as $Saccharomyces\ cerevisiae$, and filamentous fungus of, for example, the genus $Aspergillus$ such as $Aspergillus\ niger$.

When prokaryotic cells are used, there are systems using bacterial cells. $E.\ coli$ and $Bacillus\ subtilis$ are known bacterial cells.

Proteins can be obtained by transforming these cells with the desired DNA, and culturing the thus transformed cells in vitro. Cell culturing is performed according to known methods. DMEM, MEM, RPMI1640 and IMDM can be used as the culture medium. In this case, serum supplements, such as fetal calf serum (FCS), can be used together, or the culture may be performed in a serum-free medium. The pH during cultivation is preferably in the range of about 6 to 8. Culture is usually carried out at about 30 to 40° C. for about 15 to 200 hr, with the exchange of medium, aeration and agitation as the occasion demands.

On the other hand, in vivo production systems include those using animals and plants. These animals or plants are transfected with a desired DNA to produce a protein in the body of animal or plant and the protein product is collected. "Host" in this invention includes these animals and plants.

When animals are used, there are production systems using mammals and insects. Goats, pigs, sheep, mice and cattle can be used as mammals (Vicki Glaser, SPECTRUM Biotechnology Applications, 1993). In addition, when mammals are used, transgenic animals can be also used.

For example, a desired DNA is inserted in the middle of a gene encoding a protein specifically produced in milk, such as the goat β-casein, to prepare a fusion gene. A DNA fragment containing this fusion gene inserted with the desired DNA is injected into a goat embryo, which is then implanted in the uterus of a female goat. The desired protein is obtained from the milk produced by the transgenic goat born from the goat which accepted the embryo or its offspring. To increase the yield of milk containing the protein produced by the transgenic goat, a suitable hormone may be appropriately administered to transgenic goats (Ebert, K. M. et al., Bio/Technology (1994) 12, 699–702).

In addition, insects, for example, silkworm can be used. In this case, silkworms are infected with the baculovirus inserted with a desired DNA, and the desired protein is obtained from their body fluid (Susumu, M. et al., Nature (1985) 315, 592–594).

Furthermore, when plants are used, tobacco, for example, can be employed. In the case of use of tobacco, a desired DNA is inserted into a plant expression vector, for example, pMON 530, and this vector is then transferred into a bacterium such as $Agrobacterium\ tumefaciens$. A tobacco plant, for example, $Nicotiana\ tabacum$, is infected with this bacterium, from leaves of which the desired protein is obtained (Julian, K. -C. Ma et al., Eur. J. Immunol. (1994) 24, 131–138).

Proteins of this invention thus obtained can be isolated from the inside and outside of cells or hosts, and purified to essentially pure and homogeneous protein preparations. Isolation and purification of proteins can be performed using conventional isolation and purification methods for usual proteins, and are not restricted in any way. For example, proteins can be isolated and purified by appropriate selection and combination of the following tools and techniques like chromatography column, filter, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromotographies can be carried out using liquid phase chromatography, for example, HPLC, FPLC, etc. This invention also includes proteins highly purified using these purification methods.

The optional modification to the protein or the removal of partial peptide therefrom can be performed by reacting proteins before or after the purification with the appropriate protein modification enzyme. Trypsin, chymotrypsin, lysyl endopeptidase, protein kinase and glucosidase are commonly used protein modification enzymes.

This invention also includes partial peptides of the hh00149 protein (SEQ ID NO: 2). The partial peptides include, for example, those corresponding to the binding site for other proteins, such as the 149Y2H#151 protein and PDZ protein out of partial peptide sequences encoded by the hh00149 gene. These partial peptides can be used for the inhibition and so on of the signal transduction via the hh00149 protein.

Partial peptides of this invention can be prepared by genetic engineering techniques, known peptide synthesis method, or cleavage of the protein of this invention with a suitable peptidase. Peptide synthesis may be performed by either the solid phase or liquid phase synthesis method.

The present invention also relates to DNAs encoding the above-described proteins of this invention. DNAs of this invention are not only used for the production of proteins of this invention as described above but also may be applied to gene therapy, and such, for disorders caused by abnormalities of the gene encoding proteins of this invention.

cDNAs encoding the proteins of this invention can be obtained, for example, by screening human cDNA libraries using the probes described in this specification.

Other cDNAs can be obtained from different cells, tissues, organs or species by further screening cDNA libraries with those cDNAs thus obtained or fragments thereof as probes. cDNA libraries may be prepared by the method described in, for example, Sambrook, J. et al., Molecular Cloning, Cold Spring Harbor Laboratory Press (1989), or commercially available DNA libraries may be used instead.

Furthermore, the sequencing of cDNA thus obtained enables the determination of the translation region encoded by the cDNA and the elucidation of amino acid sequence of the protein of this invention. In addition, the genomic DNA can be isolated by screening the genomic DNA library with cDNAs thus obtained as probes.

Specifically, the following procedures may be used. First, mRNA is isolated from cells, tissues or organs expressing the protein of this invention. For the isolation of mRNA, the total RNA is prepared by known methods, for example, the guanidine ultracentrifugation method (Chirgwin, J. M. et al., Biochemistry (1979) 18, 5294–5299), the AGPC method (Chomczynski, P. and Sacchi, N., Anal. Biochem. (1987) 162, 156–159), and such, and mRNA is then purified from the total RNA using an mRNA Purification Kit (Pharmacia), etc. mRNA can be also directly prepared using a QuickPrep mRNA Purification Kit (Pharmacia).

cDNA is synthesized from mRNA thus obtained using the reverse transcriptase. Synthesis of cDNA can also be performed using an AMV Reverse Transcriptase First-strand cDNA Synthesis Kit (Seikagaku Kogyo). cDNA can also be synthesized and amplified according to the 5'-RACE method (Frohman, M. A. et al., Proc. Natl. Acad. Sci. USA (1988) 85, 8998–9002; Belyavsky, A. et al., Nucleic Acids Res. (1989) 17, 2919–2932) using a 5'-Ampli FINDER RACE Kit (Clontech) and the polymerase chain reaction (PCR) with probes described in this specification.

The desired DNA fragments are prepared from PCR products thus obtained, and ligated to a vector DNA. Then, a recombinant vector is prepared, transferred into E. coli, and such, and colonies are selected to prepare the desired recombinant vector. Base sequence of the desired DNA may be confirmed by known methods, for example, the dideoxynucleotide chain termination method.

Furthermore, the sequence for a higher expression efficiency can be designed for the DNA of this invention, considering the frequency of codon used by the host to be used for expression (Grantham, R. et al., Nucleic Acids Research (1981) 9, p43–74). DNAs of this invention can be modified using commercially available kits and known methods. For example, these modifications include the digestion with restriction enzymes, the insertion of synthetic oligonucleotides and suitable DNA fragments, the ligation of linkers, the insertion of the initiation codon (ATG) and/or termination codon (TAA, TGA or TAG), etc.

Specifically, the DNA of this invention includes DNAs encoding the protein comprising the amino acid sequence set forth in SEQ ID NO: 2 and mutants thereof described above. A preferred DNA comprises the base sequence extending from base 466 (A) to base 2832 (C) in the base sequence shown in SEQ ID NO: 1.

DNAs of this invention also include DNAs which hybridize under stringent conditions to the DNA consisting of the base sequence set forth in SEQ ID NO: 1, and encoding proteins functionally equivalent to the above-described proteins of this invention.

Stringent hybridization conditions can be appropriately selected by those skilled in the art, including, for example, low stringent conditions. Low stringent conditions refer to, for example, hybridization at 42° C. and washing in 2× SSC and 0.1% SDS, and preferably at 50° C. and in 2× SSC and 0.1% SDS. Yet more preferably, high stringent conditions may be selected. High stringent conditions refer to, for example, hybridization at 65° C. and washing in 2× SSC and 0.1% SDS. Under these conditions, as the hybridization temperature is elevated, DNA with a higher homology can be obtained. The above-described DNAs to be hybridized are preferably cDNA or chromosomal DNA.

Proteins of this invention are useful for screening compounds binding to protein. That is, the proteins are used in the method of screening for compounds that bind to the proteins of this invention, in which the method comprises bringing proteins of this invention into contact with a test sample that is expected to contain a compound to bind to the proteins and selecting a compound with the activity to bind to the proteins of this invention.

Proteins of this invention used in the screening may be any of recombinant, natural or partial peptides. Also they may be a purified protein, partial peptides thereof, or in the form of proteins expressed on the cell surface or membrane fractions.

Samples to be tested in the screening method of this invention may include, for example, peptides, purified or crude proteins, non-peptidic compounds, synthetic compounds, fermentation products of microorganisms, cell extracts, animal tissue extracts, marine creature extracts and plant extracts. Samples to be tested may be those naturally occurring or artificially synthesized.

Screening of proteins binding to the proteins of this invention can be carried out, for example, by the immunoprecipitation method. Specifically, the method can be carried out as follows. The gene encoding the protein of this invention is expressed by inserting the gene downstream of the promoter of foreign gene expression in pSV2neo, pcDNA I, pCD8, and such, and expressing the gene in animal cells, etc. Any generally used promoters may be employed for the expression, including the SV40 early promoter (Rigby In Williamson (ed.), Genetic Engineering, Vol. 3. Academic Press, London, p.83–141 (1982)), EF-1 α promoter (Kim, et al. Gene 91, p. 217–223 (1990)), CAG promoter (Niwa, et al. Gene 108, p. 193–200 (1991)), RSV LTR promoter (Cullen, Methods in Enzymology 152, p.684–704 (1987)), SR α promoter (Takebe et al., Mol. Cell. Biol. 8, p.466 (1988)), CMV immediate early promoter (Seed and Aruffo Proc. Natl. Acad. Sci. USA 84, p. 3365–3369 (1987)), SV40 late promoter (Gheysen and Fiers J. Mol. Appl. Genet. 1, p.385–394 (1982)), Adenovirus late promoter (Kaufman et al., Mol. Cell. Biol. 9, p.946 (1989)), HSV TK promoter, etc. Transfer of a foreign gene into animal cells for its expression can be performed by any of the following methods, including the electroporation method (Chu, G. et al., Nucl. Acid Res. 15, 1311–1326 (1987)), the calcium phosphate method (Chen, C. and Okayama, H. Mol. Cell. Biol. 7, 2745–2752 (1987)), the DEAE dextran method (Lopata, M. A. et al. Nucl. Acids Res. 12, 5707–5717 (1984); Sussman, D. J. and Milman, G. Mol. Cell. Biol. 4, 1642–1643 (1985)), the lipofectin method (Derijard, B. Cell, 7, 1025–1037 (1994); Lamb, B. T. et al. Nature Genetics 5, 22–30 (1993)), Rabindran, S. K. et al. Science 259, 230–234 (1993)), etc. The protein of this invention can be expressed as a fusion protein having the recognition site for a monoclonal antibody by introducing the recognition site (epitope) for a monoclonal antibody, the specificity of which has been established, into the N- or C-terminal of the protein of this invention. For this purpose, a commercial epitope-antibody system can be utilized (Jikken Igaku (Experimental Medicine) 13, 85–90 (1995)). Vectors are commercially available which are capable of expressing fusion proteins with β-galactosidase, maltose-binding protein, glutathione S-transferase, green fluorescence protein (GFP), and such, via the multi-cloning site.

To minimize the alteration in properties of the protein of this invention due to the fusion protein formation, there has been reported a method for preparing a fusion protein by introducing only a small epitope portion comprising several to ten amino acid residues. For example, the epitopes of polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), and such, and monoclonal antibodies to recognize these epitopes can be utilized as the epitope-antibody system for screening proteins binding to the protein of this invention (Jikken Igaku (Experimental Medicine) 13, 85–90 (1995)).

In the immunoprecipitation, immune complexes are formed by adding these antibodies to the cell lysate prepared using suitable surfactants. This immune complex comprises a protein of this invention, a protein capable of binding to the protein, and an antibody. The immunoprecipitation can also be performed using an antibody to a protein of this invention besides antibodies to the above-described epitopes. An antibody to a protein of this invention can be prepared by inserting a gene encoding a protein of this invention into an appropriate expression vector of E. coli to express it in the bacterium, purifying the protein thus expressed, and immunizing rabbits, mice, rats, goats, chicken, and such, with the purified protein. The antibody can also be prepared by immunizing the above-described animals with partial peptides of the protein of this invention.

Immune complexes can be precipitated using, for example, Protein A Sepharose and Protein G Sepharose in case that the antibody is a murine IgG antibody. In addition, in the case where the protein of this invention is prepared as a fusion protein with the epitope of, for example, GST, and such, the immune complex can be formed using a substance that specifically binds to these epitopes, such as glutathione-Sepharose 4B, and such, giving the same result as in the case where the antibody for the protein of this invention is used.

Immune precipitation, in general, may be carried out according to, or following the method described in the literature (Harlow, E. and Lane, D.: Antibodies, pp.511–552, Cold Spring Harbor Laboratory publications, New York (1988)).

SDS-PAGE is generally used for the analysis of immunoprecipitated proteins. Bound proteins can be analyzed based on the molecular weights of proteins using a gel of an appropriate concentration. In this case, although proteins bound to the protein of this invention, in general, are hardly detectable by the usual protein staining method, such as Coomassie staining and silver staining, the detection sensitivity can be improved by culturing cells in a medium containing the radio isotope-labeled $^{35}$S-methionine and $^{35}$S-cysteine to label proteins inside the cells, and detecting the labeled proteins. Once the molecular weight of the protein is determined, the desired protein can be purified directly from SDS-polyacrylamide gel and sequenced.

And, another embodiment of screening of this invention is exemplified by a method utilizing the 2-hybrid system using cells (Fields, S., and Sternglanz, R., Trends Genet. (1994) 10, 286–292).

Herein, a 2-hybrid system can be used, in which (1) an expression vector containing a first DNA encoding a fusion protein, comprising the protein of this invention and one of the subunits of a heterodimeric transcriptional regulatory factor, and (2) another expression vector containing a second DNA, comprising a desired cDNA as the test sample ligated to a DNA encoding another subunit of the heterodimeric transcriptional regulatory factor, is introduced into cells, and expressed, so that when the protein encoded by the cDNA binds to the protein of this invention to allow the transcriptional regulatory factor to form a heterodimer, the reporter gene previously constructed within the cells is expressed. Alternatively, another 2-hybrid system can be used, in which a transcriptional regulatory factor, such as the yeast GAL4 protein having a DNA-binding domain and a trans-activation domain, is separated by each domain, a first expression vector containing DNA encoding the fusion protein, comprising the DNA-binding domain of the transcriptional regulatory factor and the protein of this invention, and a second expression vector, containing DNA comprising a desired cDNA as the test sample ligated to DNA encoding the trans-activation domain of the transcriptional regulatory factor, are introduced into cells and expressed, so that when the protein encoded by the cDNA binds to the protein of this invention to allow the transcriptional regulatory factor to form a heterodimer, the reporter gene previously constructed within the cells is expressed. When there is a protein capable of binding to the protein of this invention, the protein can be sorted out by detecting or measuring the expression amount of the reporter gene.

More specifically, the process may be performed as follows. That is, DNA encoding the protein of this invention is ligated to the DNA encoding the DNA-binding domain of LexA, so that they are in the same reading frame to form a first expression vector. Next, a second expression vector is formed by ligating a desired cDNA to the gene encoding the trans-activation domain of GAL4.

After the cells integrated with the HIS3 gene the transcription of which is regulated by the promoter having the LexA-binding motif are transformed with the above-described expression plasmids of the 2-hybrid system, they are incubated in a histidine-free synthetic medium. In this case, cell growth is observed only when the interaction between proteins occurs. Thus, an increase in the expression amount of reporter gene can be assessed by the growth extent of the transformant. Besides the HIS3 gene, the Ade2 gene, the LacZ gene, and CAT gene, the luciferase gene, and such, can be used as the reporter gene.

The 2-Hybrid system can be constructed using a conventional method, or using commercial kits instead. Commercially available 2-hybrid system kits include a MATCH-MARKER Two-Hybrid System, Mammalian MATCHMAKER Two-Hybrid Assay Kit (both from CLONTECH), HybriZAP Two-Hybrid Vector System (Stratagene).

In fact, receptor-protein interactions involved in the ion channel and signal transduction having the PDZ domain have been demonstrated using the 2-hybrid system of yeast, including the binding of APC to hDLG (A. Matsumine et al. Science 272, 1020–1023 (1996)), the binding of GRIP to the AMPA receptor (H. Dong et al. Nature 386, 279–284 (1997)), the binding of Homer to the glutamate receptor (P. R. Brakeman et al. Nature 386, 284–288 (1997)), the binding of SRY to SIP-1 (F. Poulat et al. J. Biol. Chem. 272, 7167–7172 (1997)), etc.

In addition, screening of proteins binding to the protein of this invention can be also performed using the West-western blotting method (Skolnik, E. Y. et al., Cell (1991) 65, 83–90). Namely, cDNA is isolated from cells, tissues and organs in which protein capable of binding to the protein of this invention is expected to be expressed, and transferred into a phage vector, for example, ëgtll, ZAPII, and such, to prepare a cDNA library, which is then expressed on plates coated with a growth medium. The protein thus expressed is fixed on a filter, which is then reacted with the labeled, purified protein of this invention, and plaques expressing a protein bound to the protein of this invention can be detected by the label. Methods for labeling the protein of this invention include methods utilizing the binding activity of biotin and avidin, methods utilizing antibodies specifically binding to the protein of this invention, or peptides or polypeptides fused with the protein of this invention, methods utilizing the radioisotopes, methods utilizing fluorescence, etc.

Screening for compounds which bind to the protein of this invention can be also carried out using affinity chromatography. The protein of this invention is immobilized on the carrier in the affinity chromatography column, to which a test sample, which is expected to express a protein capable of binding to the protein of this invention, is applied. After applying the test sample, the column is washed, and protein which binds to the protein of this invention can be obtained.

Compounds isolated by the above-described screening method can be candidates for drugs to stimulate or suppress the activity of the protein of this invention in disorders caused by its functional abnormalities, etc. Compounds, which are obtained by the screening method of this invention and which have the activity to bind to the protein of this invention, the partial structure of which is modified by addition, deletion and/or substitution (of amino acid residues), are also included in compounds obtained by the screening method of this invention.

When compounds obtained using the screening method of this invention are used as drugs for humans and mammals, for example, mice, rats, guinea pigs, rabbits, chickens, cats, dogs, sheep, pigs, cattle, monkeys, baboons and chimpanzees, they can be administered according to commonly used means.

The compounds can be administered, as the occasion demands, orally, as sugar-coated tablets, capsules, elixirs and microcapsules, or parenterally, in the form of sterile solutions in water or other pharmaceutically acceptable liquids, or suspensions for injections. For example, drugs can be manufactured by mixing substances having the activity to bind to the protein of this invention with physiologically acceptable carriers, seasonings, excipients, vehicles, anticeptics, stabilizers and binders in the unit dosage form required in a generally accepted pharmaceutical procedure. Amounts of effective ingredients in these pharmaceutical preparations are adjusted so as to obtain the appropriate dose in the specified range.

Additives which can be mixed in tablets and capsules include, for example, binders such as gelatin, corn starch, tragacanth gum and arabic gum, excipients such as crystalline cellulose, bulking agents such as corn starch, gelatin and alginic acid, lubricants such as magnesium stearate, sweetening agents such as sucrose, lactose or saccharine, and flavors such as peppermint, *Gaultheria adenothrix* oil or cherry. When the dispensing unit form is a capsule, liquid carriers, such as oil, can be further added to the above-described materials. Sterile compositions for injection can be prescribed using vehicles such as distilled water for injection according to standard pharmaceutical procedure.

Aqueous solutions for injections include, for example, physiological saline and isotonic solutions containing glucose and other supplements such as D-sorbitol, D-mannose, D-mannitol, sodium chloride, and such, and suitable solubilizers, for example, alcohols, more specifically, ethanol, polyalcohols such as propylene glycol, polyethylene glycol, non-ionic surfactants such as polysorbate 80 (TM) and HCO-50 may be used together.

Oily solutions, including sesame oil and soybean oil, and benzyl benzoate and benzyl alcohol may be used together as the solubilizer. Injections may be combined with buffers such as phosphate buffer and sodium acetate buffer, soothing agents such as procaine hydrochloride, stabilizers such as benzyl alcohol, phenols and antioxidants. Injections thus prepared are typically filled in suitable ampules.

Though they vary depending on the symptoms, doses of compounds having the activity to bind to the protein of this invention are in the range of about 0.1 to 100 mg, preferably about 1.0 to 50 mg, and more preferably about 1.0 to 20 mg per day for adults (based on the body weight 60 kg) in the case of oral administration.

Though it varies depending on the subject to be administered, target organ, symptom and method of administration, a single dose of the compounds for the parenteral administration is preferably administered, for example, when it is in the form of injection, intravenously to normal adults (based on the body weight 60 kg) in the range of about 0.01 to 30 mg, preferably about 0.1 to 20 mg, and more preferably about 0.1 to 10 mg or thereabout per day. Doses converted on the 60 kg body weight basis can be similarly administered to other animals.

Antibodies of this invention can be obtained as monoclonal or polyclonal antibodies by known means.

Antibodies specifically binding to the protein of this invention can be prepared by immunizing suitable animals with protein used as the antigen according to a usual immunization method, fusing immunocytes thus obtained with known parent cells by a usual cell fusion method, and screening antibody-producing cells by an ordinary screening method.

Specifically, monoclonal or polyclonal antibodies which specifically binds to the protein of this invention may be prepared as follows.

For example, the protein of this invention used as the antigen for obtaining antibodies, though there is no limitation in animal species from which it is derived, is preferably a protein derived from mammals, for example, humans, mice or rats, especially from humans, which can be obtained using the gene sequence or amino acid sequence disclosed in the present specification.

In this invention, proteins having the biological activities of the proteins described in this specification can be used as the antigen. Partial peptides of these proteins can be also used as the antigen. These partial peptides of the protein include, for example, the amino (N)-terminal fragments and carboxyl terminal (C) fragments of the protein. "Antibody" as described in this specification means an antibody specifically reacting with the full length protein or fragments thereof.

After inserting the gene encoding the protein of this invention or fragments thereof into a known expression vector and transforming host cells described in this specification with this recombinant vector, the desired protein or fragments thereof are obtained from inside and outside host cells or from host cells by a standard method. These proteins may be used as the antigen. Cells expressing the protein or the lysate thereof, or the chemically synthesized protein of this invention may also be used as the antigen.

Although there is no limitation in species of mammals to be immunized with the antigen, it is preferable to take into consideration the compatibility with parent cells used for cell fusion, and animals of the rodent, lagomorph and primate are generally used.

For example, mice, rats, hamsters, and such, are used among the rodent animals, rabbits among lagomorphic animals, and monkeys among primate animals. Among monkeys, catarrhine monkeys (old world monkeys), for example, *Macaca fascicularis,* rhesus monkey, baboon, chimpanzee and such are used.

Immunization of animals with antigens is carried out according to any known method. For example, immunization in general is performed by the intraperitoneal or subcutaneous injection of the antigen to mammals. Specifically, the antigen is diluted or suspended to the appropriate amount in PBS (Phosphate-Buffered Saline) or physiological saline, mixed with suitable amount of usual adjuvant, for example, Freund's complete adjuvant, as the occasion demands, emulsified, and then administered to mammals, favorably followed by several booster injections of the antigen mixed with an appropriate amount of Freund's incomplete adjuvant every 4~21 days. In addition, suitable carriers can be used at the time of immunization with the antigen. Elevation of levels of the desired antibody in the sera of animals thus immunized is confirmed by a standard method.

Herein, polyclonal antibodies to the protein of this invention are obtained by withdrawing the blood of mammals sensitized with the antigen after confirming the elevation of levels of desired antibody in the serum, and isolating the serum from the blood by a known method. Serum containing polyclonal antibody may be used as the polyclonal antibody, or fractions containing polyclonal antibody may be further isolated from the serum as the occasion demands.

Monoclonal antibodies can be obtained by removing immunocytes from the mammals, after confirming the elevation of levels of desired antibody in the serum of mammals sensitized with the above-described antigen, and subjecting them to cell fusion. In this case, immunocytes preferably used for cell fusion are spleen cells in particular. Parent cells to be fused to the above-described immunocytes are preferably mammalian myeloma cells, more preferably myeloma cells which have acquired characteristics for the selection of fused cells by drugs.

Cell fusion of the above-described immunocytes and myeloma cells can be carried out according to a known method, for example, the method of Milstein et al. (Galfre, G. and Milstein, C., Methods Enzymol. (1981) 73, 3–46), etc.

Hybridomas thus obtained by cell fusion are selected by culturing them in a standard selection medium, for example, the HAT culture medium (culture solution containing hypoxanthine, aminopterin and thymidine). Culturing in the HAT medium is continued for a sufficient time required for killing other cells (non-fused cells) than desired hybridomas, usually for several days to several weeks. Then, a usual limiting culture-dilution method is applied for carrying out screening and cloning of hybridomas producing the desired antibody.

In addition to the above-described hybridomas obtained by immunizing animals other than humans with the antigen, human lymphocytes, for example, human lymphocytes infected with the EB virus, are sensitized with a protein, protein expressing cells or lysates thereof in vitro, and the sensitized lymphocytes are fused with human-derived myeloma cells having a permanent proliferation potency, for example, U266 cells, to obtain hybridomas capable of producing the desired human antibody having the activity to bind to the protein (Unexamined Published Japanese Patent Application No. Sho 63-17688).

Furthermore, human antibodies against a protein may be obtained by immunizing transgenic animals having a repertoire of human antibody genes with an antigen protein, cells expressing the protein or lysate thereof, to obtain antibody-producing cells, and fusing these cells to myeloma cells to prepare hybridonmas, which are used to obtain human antibody against the protein (cf. International Patent Application Nos. WO92-03918, WO93-2227, WO94-02602, WO94-25585, WO96-33735 and WO96-34096).

Besides the production of antibody using hybridoma, immunocytes, such as sensitized lymphocytes, and such, producing antibody which is immortalized with oncogenes may be used for the antibody production.

Monoclonal antibodies thus obtained can be also prepared as a recombinant antibody, using genetic recombination techniques (cf., for example, Borrebaeck, C. A. K. and Larrick, J. W., THERAPEUTIC MONOCLONAL ANTIBODIES, Published in the United Kingdom by MACMILLAN PUBLISHERS Ltd, 1990). A recombinant antibody is produced by cloning DNA encoding the protein from hybridoma or immunocytes such as sensitized lymphocytes producing the antibody, incorporating the DNA into appropriate vector, and transferring the vector into host cells. This recombinant antibody is also included in this invention.

Antibodies of this invention may also include fragments and modified products of the antibody, so long as they are capable of binding to the protein of this invention. For example, the antibody fragments include Fab, F(ab')2, Fv or a single-chained Fv (scFv) prepared by linking the H-chain to the Fv of L-chain via a suitable linker (Huston, J. S. et al., Proc. Natl. Acad. Sci. USA (1988) 85, 5879–5883). Specifically, antibody fragments are produced by digesting the antibody with enzymes, for example, papain or pepsin, or by constructing a gene encoding these fragments, inserting the gene into an expression vector, and expressing it in suitable host cells (cf., for example, Co, M. S. et al., J. Immunol. (1994) 152, 2968–2976; Better, M. and Horwitz, A. H., Methods Enzymol. (1989) 178, 476–496; Pluckthun, A. and Skerra, A., Methods Enzymol. (1989) 178, 497–515; Lamoyi, E., Methods Enzymol. (1986) 121, 652–663; Rousseaux, J. et al., Methods Enzymol. (1986) 121, 663–669; Bird, R. E. and Walker, B. W., Trends Biotechnol. (1991) 9, 132–137).

Antibody bound to various molecules, such as polyethylene glycol (PEG), and such, can also be used as the modified antibody. The "antibody" of this invention also includes these modified antibodies. These modified antibodies can be prepared by chemically modifying the antibody obtained as above. These modification methods have been already established in this field.

In addition, the antibody of this invention can be obtained, using known techniques, as a chimeric antibody comprising the variable region derived from a non-human antibody and the constant region derived from a human antibody, or a humanized antibody comprising the CDR (complementary-determining region) derived from a non-human antibody, the FR (framework region) and the constant region derived from a human antibody.

Antibodies obtained as described above can be purified to homogeneity. For the isolation and purification of the antibody used in this invention, any methods of isolation and purification used for ordinary proteins can be applied without limitation. Concentration of the antibody obtained as described above can be determined by the measurement of absorbance or the enzyme-linked immunosorbent assay (ELISA), etc.

Furthermore, ELISA, EIA (enzyme immunoassay), RIA (radioimmunoassay) or fluorescent antibody technique can be used as the methods for measuring the antigen-binding activity of the antibody of this invention. For example, when ELISA is used, the protein of this invention is added to plates on which the antibody of this invention has been immobilized, and then a sample containing the desired antibody, for example, the culture supernatant of antibody-producing cells or purified antibody is added to the plates. A secondary antibody labeled with an enzyme, for example, alkaline phosphatase and such, to recognize the antibody is added to the plates. After incubating and washing the plates, the enzyme substrate such as p-nitrophenyl phosphate, and such, is added to measure the absorbance, so that the antigen-binding activity can be assessed. In place of a whole protein, its fragments, for example, fragments comprising its C-terminal or N-terminal, may be used. For the activity assay of the antibody of this invention, BIAcore (Pharmacia) can be used.

A method for detecting and measuring the protein of this invention can be carried out by using these techniques, the method comprising bringing the antibody of this invention into contact with a sample which is expected to contain the protein of this invention, and detecting or measuring an immune complex consisting of the antibody and the protein.

Since the method of this invention for detecting or measuring proteins is capable of selectively detecting or measuring proteins, it is useful for various experiments and such, using proteins.

The present invention includes polynucleotides hybridizing to a DNA comprising a base sequence set forth in SEQ ID NO: 1 or a DNA complementary to the DNA, and consisting of at least 15 bases. That is, this invention includes probes, nucleotides or nucleotide derivatives, for example, antisense-oligonucleotides, ribozymes, and such, which are capable of selectively hybridizing to a DNA encoding the protein of this invention or a DNA complementary to the DNA.

This invention includes an antisense oligonucleotide, for example, hybridizing to any site of the base sequence set forth in SEQ ID NO: 1. This is preferably an antisense oligonucleotide to a nucleotide comprising at least 15 or more consecutive nucleotides in the base sequence set forth in SEQ ID NO: 1. More preferably, the antisense oligonucleotide comprises at least 15 or more consecutive bases containing the translation initiation codon.

Derivatives and modified products of antisense oligonucleotides can be used as the antisense oligonucleotide. Such modified products include those modified with low alkyl phosphonates, such as the methyl phosphonate type and ethyl phosphonate type, those modified with phosphorothionate or phosphoroamidate, etc.

Herein, "antisense oligonucleotide" includes not only nucleotides corresponding to those constituting a predetermined region of a DNA or mRNA of which are all complementary to the DNA or mRNA, but also nucleotides having one or a plurality of mismatched nucleotides so far as they can selectively as well be stably hybridize to the base sequence set forth in SEQ ID NO: 1.

Herein, the phrase "selectively and stably hybridize" means that a DNA does not significantly cross-hybridize to other DNAs encoding other proteins under usual hybridization conditions, preferably under a stringent hybridization conditions. Such a polynucleotide refers to the one which has a base sequence of at least 15 consecutive nucleotides, and has at least 70% or more, preferably at least 80% or more, more preferably at least 90% or more, and further more preferably at least 95% or more of base sequence identity to a nucleotide to be hybridized. Algorithms described in this specification can be used to determine the sequence homology. Such polynucleotides are useful, as described below in examples, as probes for detecting or isolating a DNA encoding the protein of this invention or as primer for amplifying the DNA.

Derivatives of antisense oligonucleotides of this invention have a suppressive effect on the action of the proteins of this invention resulting from the repression of the expression of the protein caused by their action on cells producing the protein of this invention and binding to DNA or mRNA encoding the protein to suppress the transcription or translation thereof or enhance the decomposition of mRNA.

Derivatives of antisense oligonucleotides of this invention can be mixed with appropriate bases inert to them to prepare the external preparation such as salve, cataplasm, etc.

In addition, as the occasion demands, excipients, isotonicity agents, solubilizers, stabilizers, antiseptics, soothing agents, and such, are added to the above-described derivatives to prepare tablets, powder agents, granules, capsules, liposome capsules, injection agents, liquid preparations, nasal drops, and such, and further lyophilized preparations. They can be prepared according to a standard method.

Derivatives of antisense oligonucleotides of this invention are either directly applied to the affected region of patient or intravascularly administered, for example, to patient, so that they can eventually reach the affected region. Furthermore, antisense nucleotide enclosing materials can be used to enhance the durability or membrane permeability, including liposome, poly-L-lysine, lipid, cholesterol, lipofectin, or derivatives thereof.

Doses of derivatives of antisense oligonucleotides of this invention can be appropriately adjusted according to the conditions of patients, and used in preferable amounts. For example, they can be administered in the range 0.1~100 mg/kg, preferably 0.1~50 mg/kg.

The antisense oligonucleotides of this invention inhibit the expression of the protein of this invention and, thus, are useful for suppressing its biological activities. Expression inhibitors comprising antisense oligonucleotides of this invention are useful in that they can suppress biological activities of the protein of this invention.

BRIEF DESCRIPTION OF THE DRAWINGS

FIG. 1 represents a photograph showing the results of Northern blot analysis of the hh00149 gene.

"H" in the figure represents the results of detection obtained using Human MTN Blot (CLONTECH, catalogue No. 7760-1), showing 1. heart, 2. brain, 3. placenta, 4. lung, 5. liver, 6. skeletal muscle, 7. kidney and 8. Pancreas. "H4" represents the results of detection obtained using Human MTN Blot IV (CLONTECH, catalogue No. 7766-1), showing 1. spleen, 2. thymus, 3. prostate, 4. testis, 5. uterus, 6. small intestine, 7. colon and 8. peripheral lymphocyte.

"F" represents the results of detection using Human Fetal MTN Blot II (CLONTECH, catalogue No. 7756-1), showing 1. fetal brain, 2. fetal lung, 3. fetal liver and 4. fetal kidney.

"C" represents the results of detection using Human Cancer Cell Line MTN Blot II (CLONTECH, catalogue No. 7757-1), showing 1. acute leukemia HL-60 cell, 2. HeLa cell S3, 3. chronic myelocytic leukemia K-562 cell, 4. lymphoblastic leukemia MOLT-4 cell, 5. Burkitt's lymphoma Raji cell, 6. colorectal adenocarcinoma SW-480 cell, 7. lung cancer A549 cell and 8. melanoma G361 cell, respectively.

"B2" represents the results of detection using Human Brain MTN Blot II (CLONTECH, catalogue No. 7755-1), showing 1. cerebellum, 2. cerebral cortex, 3. medulla oblongata, 4. spinal cord, 5. occipital lobe, 6. frontal lobe, 7. temporal lobe and 8. putamen, respectively.

"B4" represents the results of detection using Human Brain MTN Blot IV (CLONTECH, catalogue No. 7769-1), 1. cerebellar tonsil, 2. caudatum, 3. corpus callosum, 4. hippocampus, 5. whole brain, 6. nigra and 7. thalamus.

FIG. 2 represents photographs showing the results of RT-PCR. The first strand cDNAs used were 32 in total, derived from 1. brain, 2. heart, 3. kidney, 4. liver, 5. lung, 6. pancreas, 7. placenta, 8. skeletal muscle, 9. large intestine, 10. ovary, 11. peripheral lymphocyte, 12. prostate, 13. small intestine, 14. spleen, 15. testis, 16. thymus, 17. fetal brain, 18. fetal heart, 19. fetal kidney, 20. fetal liver, 21. fetal lung, 22. fetal skeletal muscle, 23. fetal spleen, 24. fetal thymus, 25. breast carcinoma (GI-101), 26. lung carcinoma (LX-1), 27. colon adenocarcinoma (CX-1), 28. lung carcinoma (GI-117), 29. prostatic adenocrcinoma (PC-3), 30. colon adenocarcinoma (GI-112), 31. ovarian carconoma (GI-102) and 32. pancreatic adenocarcinoma (GI-103) (CLONTECH, catalogue Nos. K1420-1, K1421-1, K1425-1, and K1422-1). Results of RT-PCR for detecting the hh-00149 gene and G3PDH gene (control) are indicated above and below, respectively.

FIG. 3 is a diagram showing an expected structure of the hh00149 protein. In this figure, the diamond-shaped mark represents a hydrophobic region, and oval-shaped mark a hydrophilic region, respectively.

BEST MODE FOR CARRYING OUT THE INVENTION

The present invention is described below in more detail with reference to examples, but is not constructed as being limited thereto.

EXAMPLE 1

Construction of Library of Size-Fractionated Human Brain cDNAs cDNAs were constructed according to the method of Ohara (DNA Research 4, 53–59 (1997)). Specifically, double-stranded cDNAs were synthesized from Human poly A+RNA whole brain (CLONTECH, catalogue No. 6516-1) using the SuperScript II reverse transcriptase (GibcoBRL, catalogue No. 18064-014) with a (dT)15 primer having the Not I site at the 5' terminal end (GACTAGTTCT AGATCGCGAG CGGCCGCCCT TTTTTTTTTT TTTT/ SEQ ID NO: 3) according to the manual. cDNAs thus obtained were digested with the restriction enzyme Not I, and then ligated to the Sal I adaptors. Sal I adaptors used are shown in Table 1.

TABLE 1

| 5'-TCGACCCACGCGTCCG-3' | (SEQ ID NO: 4) |
| 3'-GGGTGCGCAGGC$_p$-5' | (SEQ ID NO: 5) | cDNAs shorter than 3 kb were removed by electrophoresis on 1% low-melting point agarose gel, and cDNA fragments larger than 3 kb in size were ligated to the pBluescript II SK+ (STRATAGENE, catalogue No. 212205) which had been digested with Not I and Sal I, and then transferred into ElectroMax DH10B™ cells (GibcoBRL, catalogue No: 18290-015) by electroporation according to the manual. Plasmid DNAs were extracted from the independent 8×10$^6$ colonies obtained as the ampicillin-resistant colonies on agar plates by the standard alkali/SDS cytolysis method. A majority of plasmid DNAs thus obtained are the closed circular DNAs, so that their sizes fractionated by electrophoresis reflect the sizes of inserted cDNAs. Therefore, plasmid DNAs which were separated into 10 fractions on 1% agarose gel correspond to fractions separated by the size of cDNAs. Each of these fractions was separately transferred again into E. coli, and plasmids were extracted from 1×10$^6$ colonies or more per each fraction. In this case, the transformed E. coli was cultured on shaking in LB medium containing 100 μg/ml ampicillin for 3 hr. Plasmids thus extracted were confirmed of their sizes by electrophoresis, and the size selection was repeated at least twice for plasmids of 8 kb or less in size, and three times for the cDNA inserts of 8 kb or more in size to construct libraries of cDNAs fractionated by size.

EXAMPLE 2

Cloning of hh00149 Gene

Plasmid DNA was extracted from the above-described library of fractionated cDNAs, and sequenced. Plasmid DNA was extracted using the PI-100 automatic plasmid DNA extraction apparatus (Kurabo). The dye-primer cycle sequencing reaction was automatically performed by the CATALYST Turbo (Perkin-Elmer) using the ABI PRISM™ cycle-sequencing kit (Perkin-Elmer). Reaction products were electrophoresed using either ABI373A or ABI377 DNA sequencer, analyzed by the ABI sequence analysis system, INHERIT. cDNA inserts were sequenced from both terminals using the Dye-labeled M13 forward primer (Perkin-Elmer) and reverse primer (Perkin-Elmer). Furthermore, the entire base sequence of cDNA was determined using the shotgun method. The hh00149 gene was sequenced as one of the clones. The base sequence and putative amino acid sequence of hh00149 are shown in SEQ ID NOs: 1 and 2, respectively.

EXAMPLE 3

Chromosome Mapping

The locus of hh00149 gene was mapped on chromosomes using the Gene Bridge 4 Radiation Hybrid Panel (Research Genetics, Inc.). The 10× KOD dash buffer (2 μl), 2.5 mM dNTP (1.6 μl), 10 μM primer 149–2867 (CAGGGTGGGA GAAGGGGAAA GAATC/SEQ ID NO: 6) (0.8 μl), 10 μM primer 149–2944 (GAGGCCATTG ACAGGGAGAC GAAAC/SEQ ID NO: 7) (0.8 μl), seterilized water (13.4 μl) and KOD dash DNA polymerase (TOYOBO #LDP-101) (0.4 μl) were mixed, warmed at 94° C. for 5 min, and then subjected to the polymerase chain reaction (PCR) of 40 repeated cycles of 98° C. for 10 sec, 60° C. for 2 sec and 74° C. for 10 sec to amplify the gene. The results were analyzed using the analysis software downloaded from the World Wide Web (http://www.sph.umich.edu/group/statgen/software). As a result, the hh00149 gene was mapped 3.2 cR from the landmark WI-4142 on chromosome 6.

EXAMPLE 4

Tissue Specificity of hh00149 Gene Expression by Northern Blot Analysis

Northern blot analysis was performed according to the usual method, using the MTN Blot (CLONTECH, catalogue Nos.: 7760-1, 7766-1, 7756-1, 7757-1, 7755-1 and 7769-1) with an Nco I fragment (corresponding to bases 948 to 1574 in SEQ ID NO: 1) (25 ng) which had been labeled with [α á-$^{32}$P]dCTP using the Megaprime DNA labelling kit (Amersham, catalogue No. RPN1607) to serve as a probe. Prehybridization was carried out in the ExpressHyb Hybridization Solution (CLONTECH, catalogue No. 8015-2) (20 ml) at 68° C. for 30 min, and then hybridization was performed with the above-described labeled probe (2×10$^7$ cpm) similarly in the ExpressHyb Hybridization Solution (20 ml) (1×10$^6$ cpm/ml) at 68° C. for 1 hr. The filter was washed three times at room temperature for 10 min each using 2× SSC (0.3 M NaCl and 0.03 M sodium citrate (pH 7.0))/0.05% SDS) followed by further washing twice in 0.1× SSC/0.1% SDS at 50° C. for 15 min. Then a FUJI Imaging plate (Fuji film) was exposed to the filter overnight, and analyzed using the FUJI BAS2000 (Fuji Film). As a result, a transcription product of 3.2 kb was specifically detected in the brain, and found to be strongly expressed, as the result of analysis using the Human Brain MTN Blot II (catalogue No.: 7755-1) and Human Brain MTN Blot IV (catalogue No.: 7769-1), in the cerebral cortex, occipital lobe, frontal lobe and temporal lobe, and also to be expressed in the cerebellum, putamen and cerebellar tonsil. Besides the brain, its expression was confirmed also in the spleen, testis, and lung cancer A549 cells (FIG. 1).

EXAMPLE 5

RT-PCR Analysis of Tissue Specificity of hh00149 Gene Expression

The expression amount of mRNA in 32 different tissues including those which had been analyzed by Northern blot was compared by RT-PCR to analyze the tissue specificity of the hh00149 gene expression. cDNAs used were the Human MTC Panel I (K1402-1), Human MTC Panel II (K1421-1), Human Fetal MTC Panel I (K1425-1) and Human Tumor MTC Panel I (K1422-1) commercially available from CLONTECH. The 10× KOD dash buffer (2 μl), 2.5 mM dNTP (1.6 μl), 10 μM primer 149–2867 (CAGGGTGGGA GAAGGGGAAA GAATC/SEQ ID NO: 6) (0.8 μl), 10 μM primer 149–2944 (GAGGCCATTG ACAGGGAGAC GAAAC/SEQ ID NO: 7) (0.8 μl), sterilized water (13.4 μl) and KOD dash DNA polymerase (TOYOBO #LDP-101) (0.4 μl) were mixed, warmed at 94° C. for 5 min, and then subjected to the polymerase chain reaction (PCR) of 30 repeated cycles at 98° C. for 10 sec, 60° C. for 2 sec and 74° C. for 10 sec. The results are shown in FIG. 2. Considerable high level of the gene expression was detected in the adult and fetal brains. The gene expression was also detected in the testis, spleen and ovary, but in no other tissues.

EXAMPLE 6

Prediction of hh00149 Protein Structure

The structure of the hh00149 protein was predicted using "peptide structure" and "pepplot" of the GCG Sequence Analysis Software Package (Genetic Computer Group, Oxford Molecular Group, Inc.) (FIG. 3). As a result, the amino acid sequence at the amino terminal (amino acids 1 to 20) and that (amino acids 527 to 557) are abundant in hydrophobicity, the former of which is thought to function as the signal sequence, and the latter as the transmembrane region.

INDUSTRIAL APPLICABILITY

Since the membrane protein of this invention is indicated to function as a signal transducer molecule from outside to inside the cell in the brain, the membrane protein and the gene thereof are expected to be used for screening novel signal transducing substances, including neuropeptides. The membrane protein of this invention and gene thereof are expected to be applied in the development of novel remedies and diagnostics for nerve-related disorders.

What is claimed is:

1. An isolated protein comprising the amino acid sequence set forth in SEQ ID NO: 2.

2. An isolated protein consisting of the amino acid sequence of SEQ ID NO: 2.

3. An isolated protein comprising amino acids 21 to 789 of SEQ ID NO: 2.

4. An isolated protein consisting of amino acids 21 to 789 of SEQ ID NO: 2.

* * * * *

UNITED STATES PATENT AND TRADEMARK OFFICE
CERTIFICATE OF CORRECTION

PATENT NO. : 6,852,836 B1  Page 1 of 1
APPLICATION NO. : 09/831846
DATED : February 8, 2005
INVENTOR(S) : Shin-ichi Funahashi et al.

It is certified that error appears in the above-identified patent and that said Letters Patent is hereby corrected as shown below:

On the title page, in Item (73), Assignees:

Replace "Sieyaku" with --Seiyaku--

At column 14, line 46:

Replace "antigen" with --antigenic--

At column 18, line 10:

Replace "constructed" with --construed--

At column 19, line 24:

Replace "seterilized" with --sterilized--

Signed and Sealed this

Fifteenth Day of May, 2007

JON W. DUDAS
*Director of the United States Patent and Trademark Office*

SEQUENCE LISTING

<160> NUMBER OF SEQ ID NOS: 7

<210> SEQ ID NO 1
<211> LENGTH: 3144

```
<212> TYPE: DNA
<213> ORGANISM: Homo sapiens
<220> FEATURE:
<221> NAME/KEY: CDS
<222> LOCATION: (466)..(2832)

<400> SEQUENCE: 1
gcctggctcc ctctcgctga gacacacata cactcacaca tacacaaccc ggcaggctcg     60
tctgaacttg aagacacccc acattccaag atgcccgagg ttcctgggaa tgcctggggt    120
tcttcgatcc ggaaaatcct accggcatcc tcctagggag ggattattat tattattttt    180
ctttaatctg gaagagaaga gaacaagttg tgcttttccc ccttcttct tgctaaacgc     240 catggatata actgaataag cggctcaggg ctttccccgc gtggacgtcc gaggccacca    300
tctgcctgca ttcgccggag ccgccggagg gtttagctcg agtctgtctc gggcggggaa    360
ggatgcgtgg ccgagccggg gagcccgggc gccccgcgga gccggcctcg gtgccaccca    420
gccgggggta gatgctgcct cgcccaggcg ctgagtgacc agacc atg gag acc ctg     477
                                                  Met Glu Thr Leu
                                                   1
```

| | | |
|---|---|---|
| ctt ggt ggc ctg cta gcg ttt ggc atg gcg ttt gcc gtg gtc gac gcc | 525 |
| Leu Gly Gly Leu Leu Ala Phe Gly Met Ala Phe Ala Val Val Asp Ala | |
| 5                    10                  15                  20 | |

```
tgc ccc aag tac tgt gtc tgc cag aat ctg tct gag tca ctg ggg acc    573
Cys Pro Lys Tyr Cys Val Cys Gln Asn Leu Ser Glu Ser Leu Gly Thr
             25                  30                  35 ctg tgc ccc tcc aag ggg ctg ctc ttt gta ccc cct gat att gac cgg    621
Leu Cys Pro Ser Lys Gly Leu Leu Phe Val Pro Pro Asp Ile Asp Arg
        40                  45                  50 cgg aca gtg gag ctg cgc ctg ggc ggc aac ttc atc atc cac atc agc    669
Arg Thr Val Glu Leu Arg Leu Gly Gly Asn Phe Ile Ile His Ile Ser
55                  60                  65 cgc cag gac ttt gcc aac atg acg ggg ctg gtg gac ctg acc ctg tcc    717
Arg Gln Asp Phe Ala Asn Met Thr Gly Leu Val Asp Leu Thr Leu Ser
        70                  75                  80 agg aac acc atc agc cac atc cag ccc ttt tcc ttt ctg gac ctc gag    765
Arg Asn Thr Ile Ser His Ile Gln Pro Phe Ser Phe Leu Asp Leu Glu
85                  90                  95                  100 agc ctc cgc tcc ctg cat ctt gac agc aat cgg ctg cca agc ctt ggg    813
Ser Leu Arg Ser Leu His Leu Asp Ser Asn Arg Leu Pro Ser Leu Gly
                105                 110                 115 gag gac acc ctc cgg ggc ctg gtc aac ctg cag cac ctt atc gtg aac    861
Glu Asp Thr Leu Arg Gly Leu Val Asn Leu Gln His Leu Ile Val Asn
            120                 125                 130 aac aac cag ctg ggc ggc atc gca gat gag gct ttt gag gac ttc ctg    909
Asn Asn Gln Leu Gly Gly Ile Ala Asp Glu Ala Phe Glu Asp Phe Leu
        135                 140                 145 ctg aca ttg gag gat ctg gac ctc tcc tac aac aac ctc cat ggc ctg    957
Leu Thr Leu Glu Asp Leu Asp Leu Ser Tyr Asn Asn Leu His Gly Leu
150                 155                 160 ccg tgg gac tcc gtg cga cgc atg gtc aac ctc cac cag ctg agc ctg   1005
Pro Trp Asp Ser Val Arg Arg Met Val Asn Leu His Gln Leu Ser Leu
165                 170                 175                 180 gac cac aac ctg ctg gat cac atc gcc gag ggc acc ttt gca gac ctg   1053
Asp His Asn Leu Leu Asp His Ile Ala Glu Gly Thr Phe Ala Asp Leu
                185                 190                 195 cag aaa ctg gcc cgc ctg gat ctc acc tcc aat cgg ctg cag aag ctg   1101
Gln Lys Leu Ala Arg Leu Asp Leu Thr Ser Asn Arg Leu Gln Lys Leu
            200                 205                 210 ccc cct gat ccc atc ttt gcc cgc tcc cag gct tcg gct ttg aca gcc   1149
Pro Pro Asp Pro Ile Phe Ala Arg Ser Gln Ala Ser Ala Leu Thr Ala
```

-continued

```
    Pro Pro Asp Pro Ile Phe Ala Arg Ser Gln Ala Ser Ala Leu Thr Ala
            215                 220                 225 aca ccc ttt gcc cca ccc ttg tcc ttt agt ttt ggg ggt aac cca ctt        1197
Thr Pro Phe Ala Pro Pro Leu Ser Phe Ser Phe Gly Gly Asn Pro Leu
            230                 235                 240 cac tgc aat tgt gag ctt ctc tgg ctg cgg agg ctc gag cgg gac gat        1245
His Cys Asn Cys Glu Leu Leu Trp Leu Arg Arg Leu Glu Arg Asp Asp
245                 250                 255                 260 gac ctg gaa acc tgt ggc tcc cca ggg ggc ctc aag ggt cgc tac ttc        1293
Asp Leu Glu Thr Cys Gly Ser Pro Gly Gly Leu Lys Gly Arg Tyr Phe
                265                 270                 275 tgg cat gtg cgt gag gag gag ttt gtg tgc gag ccg cct ctc atc acc        1341
Trp His Val Arg Glu Glu Glu Phe Val Cys Glu Pro Pro Leu Ile Thr
            280                 285                 290 cag cac aca cac aag ttg ctg gtt ctg gag ggc cag gcg gcc aca ctc        1389
Gln His Thr His Lys Leu Leu Val Leu Glu Gly Gln Ala Ala Thr Leu
            295                 300                 305 aag tgc aaa gcc att ggg gac ccc agc ccc ctt atc cac tgg gta gcc        1437
Lys Cys Lys Ala Ile Gly Asp Pro Ser Pro Leu Ile His Trp Val Ala
310                 315                 320 ccc gat gac cgc ctg gta ggg aac tcc tca agg acc gct gtc tat gac        1485
Pro Asp Asp Arg Leu Val Gly Asn Ser Ser Arg Thr Ala Val Tyr Asp
325                 330                 335                 340 aat ggc acc ctg gac atc ttc atc acc aca tct cag gac agt ggt gcc        1533
Asn Gly Thr Leu Asp Ile Phe Ile Thr Thr Ser Gln Asp Ser Gly Ala
                345                 350                 355 ttc acc tgc att gct gcc aat gct gcc gga gag gcc acg gcc atg gtg        1581
Phe Thr Cys Ile Ala Ala Asn Ala Ala Gly Glu Ala Thr Ala Met Val
            360                 365                 370 gag gtc tcc atc gtc cag ctg cca cac ctc agc aac agc acc agc cgc        1629
Glu Val Ser Ile Val Gln Leu Pro His Leu Ser Asn Ser Thr Ser Arg
            375                 380                 385 act gca ccc ccc aag tcc cgc ctc tca gac atc act ggc tcc agc aag        1677
Thr Ala Pro Pro Lys Ser Arg Leu Ser Asp Ile Thr Gly Ser Ser Lys
            390                 395                 400 acc agc cgg gga ggt gga ggc agt ggg ggc gga gag cct ccc aaa agc        1725
Thr Ser Arg Gly Gly Gly Gly Ser Gly Gly Gly Glu Pro Pro Lys Ser
405                 410                 415                 420 ccc ccg gaa cgg gct gtg ctt gtg tct gaa gtg acc acc acc tcg gcc        1773
Pro Pro Glu Arg Ala Val Leu Val Ser Glu Val Thr Thr Thr Ser Ala
                425                 430                 435 ctg gtc aag tgg tct gtc agc aag tca gca ccc cgg gtg aag atg tac        1821
Leu Val Lys Trp Ser Val Ser Lys Ser Ala Pro Arg Val Lys Met Tyr
            440                 445                 450 cag ctg cag tac aac tgc tct gac gat gag gta ctg att tac agg atg        1869
Gln Leu Gln Tyr Asn Cys Ser Asp Asp Glu Val Leu Ile Tyr Arg Met
            455                 460                 465 atc cca gcc tcc aac aag gcc ttc gtg gtc aac aac ctg gtg tca ggg        1917
Ile Pro Ala Ser Asn Lys Ala Phe Val Val Asn Asn Leu Val Ser Gly
            470                 475                 480 act ggc tac gac ttg tgt gtg ctg gcc atg tgg gat gac aca gcc acg        1965
Thr Gly Tyr Asp Leu Cys Val Leu Ala Met Trp Asp Asp Thr Ala Thr
485                 490                 495                 500 aca ctc acg gcc acc aac atc gtg ggc tgc gcc cag ttc ttc acc aag        2013
Thr Leu Thr Ala Thr Asn Ile Val Gly Cys Ala Gln Phe Phe Thr Lys
                505                 510                 515 gct gac tac ccg cag tgc cag tcc atg cac agc cag att ctg ggc ggc        2061
Ala Asp Tyr Pro Gln Cys Gln Ser Met His Ser Gln Ile Leu Gly Gly
            520                 525                 530
```

```
acc atg atc ctg gtc atc ggg ggc atc atc gtg gcc acg ctg ctg gtc    2109
Thr Met Ile Leu Val Ile Gly Gly Ile Ile Val Ala Thr Leu Leu Val
        535                 540                 545 ttc atc gtc atc ctc atg gtg cgc tac aag gtc tgc aac cac gag gcc    2157
Phe Ile Val Ile Leu Met Val Arg Tyr Lys Val Cys Asn His Glu Ala
550                 555                 560 ccc agc aag atg gca gcg gcc gtg agc aat gtg tac tcg cag acc aac    2205
Pro Ser Lys Met Ala Ala Ala Val Ser Asn Val Tyr Ser Gln Thr Asn
565                 570                 575                 580 ggc gcc cag cca ccg cct cca agc agc gca cca gcc ggg gcc ccg ccg    2253
Gly Ala Gln Pro Pro Pro Pro Ser Ser Ala Pro Ala Gly Ala Pro Pro
                585                 590                 595 cag ggc ccg ccg aag gtg gtg gtg cgc aac gag ctc ctg gac ttc acc    2301
Gln Gly Pro Pro Lys Val Val Val Arg Asn Glu Leu Leu Asp Phe Thr
            600                 605                 610 gcc agc ctg gcc cgc gcc agt gac tcc tct tcc tcc agc tcc ctg ggc    2349
Ala Ser Leu Ala Arg Ala Ser Asp Ser Ser Ser Ser Ser Ser Leu Gly
        615                 620                 625 agt ggg gag gct gcg ggg ctg gga cgg gcc ccc tgg agg atc cca ccc    2397
Ser Gly Glu Ala Ala Gly Leu Gly Arg Ala Pro Trp Arg Ile Pro Pro
    630                 635                 640 tcc gcc ccg cgc ccc aag ccc agc ctt gac cgc ctg atg ggg gcc ttc    2445
Ser Ala Pro Arg Pro Lys Pro Ser Leu Asp Arg Leu Met Gly Ala Phe
645                 650                 655                 660 gcc tcc ctg gac ctc aag agt cag aga aag gag gag ctg ctg gac tcc    2493
Ala Ser Leu Asp Leu Lys Ser Gln Arg Lys Glu Glu Leu Leu Asp Ser
                665                 670                 675 agg act cca gcc ggg aga ggg gct ggg acg tcg gcc cgg ggc cac cac    2541
Arg Thr Pro Ala Gly Arg Gly Ala Gly Thr Ser Ala Arg Gly His His
            680                 685                 690 tcg gac cga gag cca ctg ctg ggg ccc cct gcg gcc cgg gcc agg agc    2589
Ser Asp Arg Glu Pro Leu Leu Gly Pro Pro Ala Ala Arg Ala Arg Ser
        695                 700                 705 ctg ctc ccc ttg ccg ttg gag ggc aag gcc aaa cgc agc cac tcc ttc    2637
Leu Leu Pro Leu Pro Leu Glu Gly Lys Ala Lys Arg Ser His Ser Phe
    710                 715                 720 gac atg ggg gac ttt gct gct gcg gcg gcg gga ggg gtc gtg ccg ggc    2685
Asp Met Gly Asp Phe Ala Ala Ala Ala Ala Gly Gly Val Val Pro Gly
725                 730                 735                 740 ggc tac agt cct cct cgg aag gtc tcg aac atc tgg acg aag cgc agc    2733
Gly Tyr Ser Pro Pro Arg Lys Val Ser Asn Ile Trp Thr Lys Arg Ser
                745                 750                 755 ctc tct gtc aac ggc atg ctc ttg ccc ttt gag gag agt gac ctg gtg    2781
Leu Ser Val Asn Gly Met Leu Leu Pro Phe Glu Glu Ser Asp Leu Val
            760                 765                 770 ggg gcc cgg ggg act ttt ggc agc tcc gaa tgg gtg atg gag agc acg    2829
Gly Ala Arg Gly Thr Phe Gly Ser Ser Glu Trp Val Met Glu Ser Thr
        775                 780                 785 gtc taggtggggg tgggcatgct cccttcctg tgcgcagggt gggagaaggg           2882
Val gaaagaatct cactggcaag tgtttgtgga gtttccatgg tgatgtttac atccagggac   2942
agtttcgtct ccctgtcaat ggcctcgtgt ccccccctac cccgcaacac ccacatcacc   3002
tccccaccac ccggccgggg tgtgctcagg gaatgtggac tcgctcaaat gccggactga   3062
gccctgagtg tttggaaagg cgagactccg ccttctaat cacaaatgta gcctacaagc    3122
aagcggcttt ggattgctta tg                                            3144

<210> SEQ ID NO 2
```

```
<211> LENGTH: 789
<212> TYPE: PRT
<213> ORGANISM: Homo sapiens

<400> SEQUENCE: 2

Met Glu Thr Leu Leu Gly Gly Leu Leu Ala Phe Gly Met Ala Phe Ala
 1               5                  10                  15

Val Val Asp Ala Cys Pro Lys Tyr Cys Val Cys Gln Asn Leu Ser Glu
                20                  25                  30

Ser Leu Gly Thr Leu Cys Pro Ser Lys Gly Leu Leu Phe Val Pro Pro
            35                  40                  45

Asp Ile Asp Arg Arg Thr Val Glu Leu Arg Leu Gly Asn Phe Ile
 50                  55                  60

Ile His Ile Ser Arg Gln Asp Phe Ala Asn Met Thr Gly Leu Val Asp
 65                  70                  75                  80

Leu Thr Leu Ser Arg Asn Thr Ile Ser His Ile Gln Pro Phe Ser Phe
                85                  90                  95

Leu Asp Leu Glu Ser Leu Arg Ser Leu His Leu Asp Ser Asn Arg Leu
            100                 105                 110

Pro Ser Leu Gly Glu Asp Thr Leu Arg Gly Leu Val Asn Leu Gln His
            115                 120                 125

Leu Ile Val Asn Asn Asn Gln Leu Gly Gly Ile Ala Asp Glu Ala Phe
130                 135                 140

Glu Asp Phe Leu Leu Thr Leu Glu Asp Leu Asp Leu Ser Tyr Asn Asn
145                 150                 155                 160

Leu His Gly Leu Pro Trp Asp Ser Val Arg Arg Met Val Asn Leu His
                165                 170                 175

Gln Leu Ser Leu Asp His Asn Leu Leu Asp His Ile Ala Glu Gly Thr
            180                 185                 190

Phe Ala Asp Leu Gln Lys Leu Ala Arg Leu Asp Leu Thr Ser Asn Arg
            195                 200                 205

Leu Gln Lys Leu Pro Pro Asp Pro Ile Phe Ala Arg Ser Gln Ala Ser
210                 215                 220

Ala Leu Thr Ala Thr Pro Phe Ala Pro Leu Ser Phe Ser Phe Gly
225                 230                 235                 240

Gly Asn Pro Leu His Cys Asn Cys Glu Leu Leu Trp Leu Arg Arg Leu
                245                 250                 255

Glu Arg Asp Asp Asp Leu Glu Thr Cys Gly Ser Pro Gly Gly Leu Lys
            260                 265                 270

Gly Arg Tyr Phe Trp His Val Arg Glu Glu Glu Phe Val Cys Glu Pro
            275                 280                 285

Pro Leu Ile Thr Gln His Thr His Lys Leu Leu Val Leu Glu Gly Gln
290                 295                 300

Ala Ala Thr Leu Lys Cys Lys Ala Ile Gly Asp Pro Ser Pro Leu Ile
305                 310                 315                 320

His Trp Val Ala Pro Asp Asp Arg Leu Val Gly Asn Ser Ser Arg Thr
                325                 330                 335

Ala Val Tyr Asp Asn Gly Thr Leu Asp Ile Phe Ile Thr Thr Ser Gln
            340                 345                 350

Asp Ser Gly Ala Phe Thr Cys Ile Ala Ala Asn Ala Ala Gly Glu Ala
            355                 360                 365

Thr Ala Met Val Glu Val Ser Ile Val Gln Leu Pro His Leu Ser Asn
370                 375                 380

Ser Thr Ser Arg Thr Ala Pro Pro Lys Ser Arg Leu Ser Asp Ile Thr
```

```
385                 390                 395                 400
Gly Ser Ser Lys Thr Ser Arg Gly Gly Gly Ser Gly Gly Gly Glu
                405                 410                 415
Pro Pro Lys Ser Pro Glu Arg Ala Val Leu Val Ser Glu Val Thr
                420                 425                 430
Thr Thr Ser Ala Leu Val Lys Trp Ser Val Ser Lys Ser Ala Pro Arg
                435                 440                 445
Val Lys Met Tyr Gln Leu Gln Tyr Asn Cys Ser Asp Asp Glu Val Leu
        450                 455                 460
Ile Tyr Arg Met Ile Pro Ala Ser Asn Lys Ala Phe Val Val Asn Asn
465                 470                 475                 480
Leu Val Ser Gly Thr Gly Tyr Asp Leu Cys Val Leu Ala Met Trp Asp
                485                 490                 495
Asp Thr Ala Thr Thr Leu Thr Ala Thr Asn Ile Val Gly Cys Ala Gln
                500                 505                 510
Phe Phe Thr Lys Ala Asp Tyr Pro Gln Cys Gln Ser Met His Ser Gln
                515                 520                 525
Ile Leu Gly Gly Thr Met Ile Leu Val Ile Gly Ile Ile Val Ala
        530                 535                 540
Thr Leu Leu Val Phe Ile Val Ile Leu Met Val Arg Tyr Lys Val Cys
545                 550                 555                 560
Asn His Glu Ala Pro Ser Lys Met Ala Ala Val Ser Asn Val Tyr
                565                 570                 575
Ser Gln Thr Asn Gly Ala Gln Pro Pro Pro Ser Ser Ala Pro Ala
                580                 585                 590
Gly Ala Pro Pro Gln Gly Pro Pro Lys Val Val Arg Asn Glu Leu
                595                 600                 605
Leu Asp Phe Thr Ala Ser Leu Ala Arg Ala Ser Asp Ser Ser Ser
                610                 615                 620
Ser Ser Leu Gly Ser Gly Glu Ala Ala Gly Leu Gly Arg Ala Pro Trp
625                 630                 635                 640
Arg Ile Pro Pro Ser Ala Pro Arg Pro Lys Pro Ser Leu Asp Arg Leu
                645                 650                 655
Met Gly Ala Phe Ala Ser Leu Asp Leu Lys Ser Gln Arg Lys Glu Glu
                660                 665                 670
Leu Leu Asp Ser Arg Thr Pro Ala Gly Arg Gly Ala Gly Thr Ser Ala
                675                 680                 685
Arg Gly His His Ser Asp Arg Glu Pro Leu Leu Gly Pro Ala Ala
                690                 695                 700
Arg Ala Arg Ser Leu Leu Pro Leu Pro Leu Glu Gly Lys Ala Lys Arg
705                 710                 715                 720
Ser His Ser Phe Asp Met Gly Asp Phe Ala Ala Ala Ala Gly Gly
                725                 730                 735
Val Val Pro Gly Gly Tyr Ser Pro Pro Arg Lys Val Ser Asn Ile Trp
                740                 745                 750
Thr Lys Arg Ser Leu Ser Val Asn Gly Met Leu Leu Pro Phe Glu Glu
                755                 760                 765
Ser Asp Leu Val Gly Ala Arg Gly Thr Phe Gly Ser Ser Glu Trp Val
                770                 775                 780
Met Glu Ser Thr Val
785
```

<210> SEQ ID NO 3

```
-continued

<211> LENGTH: 44
<212> TYPE: DNA
<213> ORGANISM: Artificial Sequence
<220> FEATURE:
<223> OTHER INFORMATION: Description of Artificial Sequence: an
      artificially synthesized primer sequence.

<400> SEQUENCE: 3
gactagttct agatcgcgag cggccgccct tttttttttt tttt          44

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: an
      artificially synthesized adapter sequence.

<400> SEQUENCE: 4
tcgacccacg cgtccg                                         16

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: an
      artificially synthesized adapter sequence.

<400> SEQUENCE: 5
cggacgcgtg gg                                             12

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: an
      artificially synthesized primer sequence.

<400> SEQUENCE: 6
cagggtggga gaagggggaaa gaatc                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: an
      artificially synthesized primer sequence.

<400> SEQUENCE: 7
gaggccattg acagggagac gaaac                               25
```